United States Patent [19]

Arena

[11] Patent Number: 4,503,274
[45] Date of Patent: * Mar. 5, 1985

[54] RUTHENIUM HYDROGENATION CATALYST WITH INCREASED ACTIVITY

[75] Inventor: Blaise J. Arena, Des Plaines, Ill.

[73] Assignee: UOP Inc., Des Plaines, Ill.

[*] Notice: The portion of the term of this patent subsequent to Apr. 19, 2000 has been disclaimed.

[21] Appl. No.: 521,465

[22] Filed: Aug. 8, 1983

[51] Int. Cl.$^3$ .................... C07C 29/132; C07C 29/14; C07C 31/26

[52] U.S. Cl. ...................................... 568/863; 502/327

[58] Field of Search .......................................... 568/863

[56] References Cited

U.S. PATENT DOCUMENTS

| | | | |
|---|---|---|---|
| 3,963,788 | 6/1976 | Kruse et al. | 568/863 |
| 3,963,789 | 6/1976 | Kruse et al. | 568/863 |
| 4,326,072 | 4/1982 | Kruse et al. | 568/863 |
| 4,380,680 | 4/1983 | Arena | 568/863 |
| 4,382,150 | 5/1983 | Arena | 568/863 |
| 4,413,152 | 11/1983 | Arena | 568/863 |

Primary Examiner—J. E. Evans
Attorney, Agent, or Firm—James R. Hoatson, Jr.; Eugene I. Snyder; William H. Page, II

[57] ABSTRACT

The reduction of an aqueous solution of a carbohydrate to its polyols using as a catalyst zerovalent ruthenium on a hydrothermally stable support can be further improved using the catalyst resulting from production of zerovalent ruthenium by reduction in hydrogen at a temperature in the range 100°–300° C. Reduction of a ruthenium compound to afford zerovalent ruthenium at these lower temperatures affords a more active catalyst.

10 Claims, 1 Drawing Figure

Catalyst Activity In Reduction Of Glucose

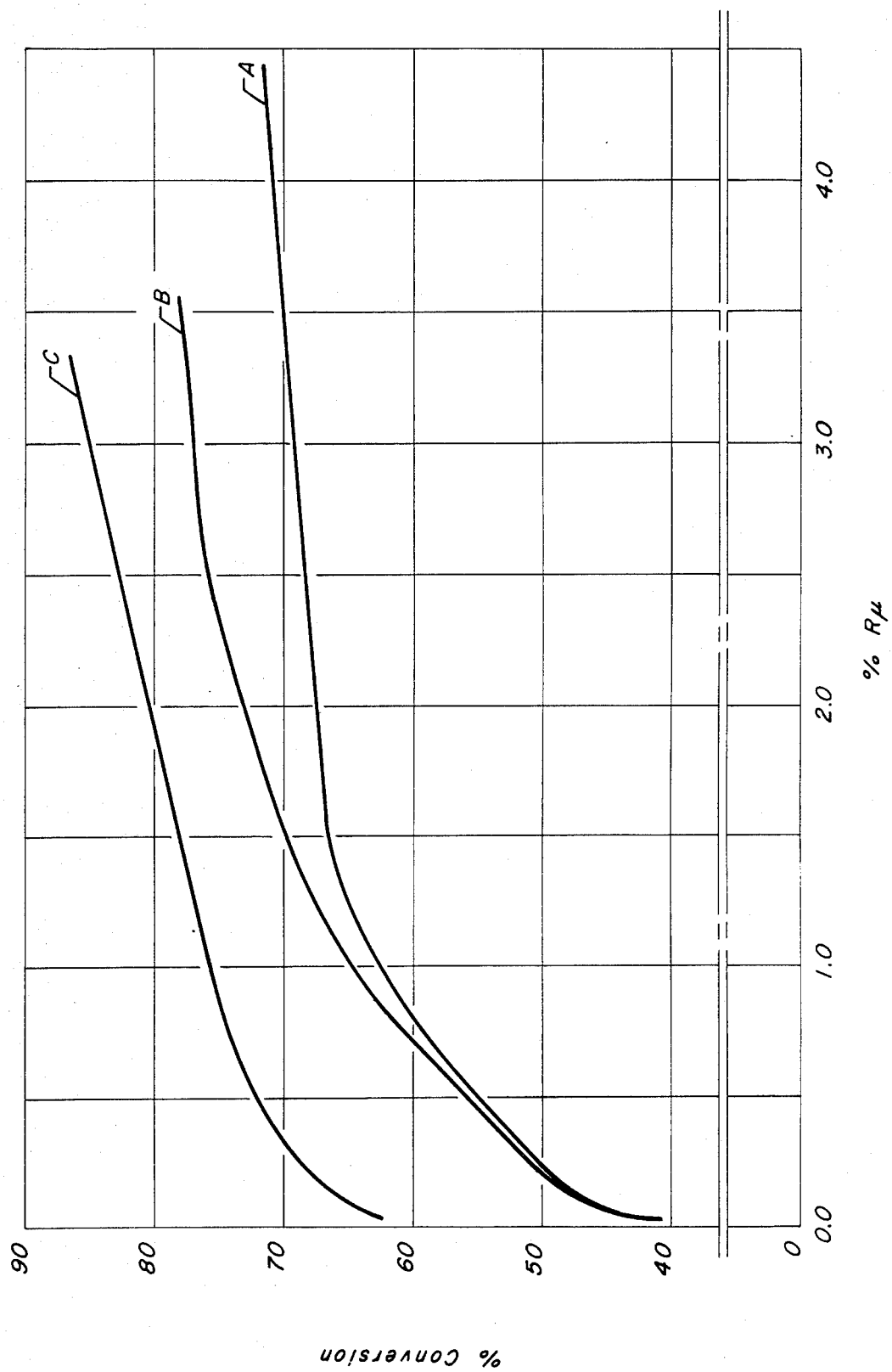

4,503,274

RUTHENIUM HYDROGENATION CATALYST WITH INCREASED ACTIVITY

BACKGROUND OF THE INVENTION

In hydrogenating organic materials using zerovalent metal catalysts, it is more common to use the metal dispersed on an inert support than to use, for example, colloidal dispersions of the metal itself. Included among advantages accruing to supported metals are their greater surface area, leading to increased reactivity, and their greater ease of separation, as by filtration. Colloidal metals are notoriously difficult to separate by filtration, and incomplete removal and recovery is costly and often deleterious to the product of hydrogenation.

When hydrogenations are conducted in aqueous media, the lack of hydrothermal stability of the commonly used supports places severe limitations on catalyst lifetime and recovery and also on the quality of the product due to dissolved support material. Where such hydrogenations are of hydroxylic organic compounds, the problem of hydrothermal instability of support materials is intensified. Where the organic compounds are polyhydroxylic, such as carbohydrates, the problem of hydrothermal instability is particularly exacerbated because of the relatively high concentration of hydroxyl groups from both water as solvent and the material to be hydrogenated.

The irony in hydrogenating aqueous solutions of carbohydrates is two-fold. First, the reduction products of many carbohydrates are important materials of commerce; sorbitol and mannitol are but two common reduction products. Second, there is no practical alternative to using water as the solvent in hydrogenating carbohydrates because carbohydrates generally are insoluble or, at best, sparingly soluble in most organic solvents. Because carbohydrates are solids, it is operationally mandatory to use a solvent in their hydrogenation.

I have previously disclosed a general method of hydrogenating carbohydrates in aqueous solution using as a catalyst zerovalent ruthenium dispersed on a hydrothermally stable support. I now disclose the further discovery that the activity of the aforementioned catalyst can be substantially increased if the zerovalent ruthenium is prepared by reduction with hydrogen of a ruthenium compound at a lower temperature than is conventionally used. Additionally, still further increased activity is achieved when the ruthenium salt dispersed on the support is not calcined prior to its reduction, also contrary to the conventional method of preparation.

DESCRIPTION OF THE FIGURE

The FIGURE shows the percent conversion of glucose in a standard activity test, as described in Example 3, vs. ruthenium content of various catalysts. The catalysts differed in their calcination treatment and reduction temperature, and are described in Example 1.

DESCRIPTION OF THE INVENTION

The invention which is the subject matter herein is a method for the hydrogenation of a carbohydrate in aqueous solution to its polyols comprising contacting at hydrogenation conditions a reaction medium consisting essentially of said solution with hydrogen and a catalyst consisting essentially of ruthenium dispersed on a hydrothermally stable support and recovering the formed polyols, where the improvement consists in producing the zerovalent ruthenium by reducing a ruthenium compound at a temperature from about 100° C. to aout 300° C.

This invention utilizes my prior discovery that certain materials commonly used as catalyst supports manifest remarkable hydrothermal stability under conditions necessary for the hydrogenation of aqueous solutions of carbohydrates, especially in comparison with the more commonly used silica and gamma-alumina. See, e.g., U.S. Pat. Nos. 4,380,680 and 4,382,150. Thus, whereas substantial amounts of silica and gamma-alumina dissolve in the aqueous medium during hydrogenation of carbohydrates, virtually no leaching of the supports used herein occurs under comparable hydrogenation conditions.

Therefore, one advantage of the claimed method is that the product contains a substantially lower level of dissolved metal from the inert support described herein than that resulting from inert supports commonly employed previously in the hydrogenation of aqueous solutions of carbohydrates.

An advantage of the use of zerovalent ruthenium as the catalyst is that of the Group VIII metals ruthenium is more resistant to leaching under hydrogenation conditions than other Group VIII metals. Because ruthenium is both resistant to leaching and particularly catalytically active it is especially advantageous in the practice of hydrogenating an aqueous solution of a carbohydrate to its polyols.

The improvement which is the invention herein is based on the discovery that zerovalent ruthenium produced by reduction in hydrogen of a suitable ruthenium compound exhibits enhanced catalytic activity when the reduction is effected in the temperature range from about 100° to about 300° C. relative to its activity when reduction is effected at the higher temperatures which presently are conventional. Thus, the invention herein has the combined advantages of affording a product with low levels of dissolved metal from the inert support, low levels of ruthenium from the catalyst, and increased catalytic activity.

The invention herein is concerned with a method of hydrogenating a carbohydrate to its polyols. Carbohydrates are polyhydroxyaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosaccharide molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention, and among these the hexoses, pentoses and tetroses are the most important members, with the hexoses particularly preferred.

The polyol reduction products of this invention have the formula $HOCH_2(CHOH)_nCH_2OH$, where n is 2, 3, or 4 depending upon the kind of monosaccharide used or the kind of units in the di- or polysaccharide. Where n is 4, the polyol is a hexitol; where n is 3, the polyol is a pentitol; and where n is 2, the polyol is a tetritol. It is to be understood that where the carbohydrate is a disaccharide or polysaccharide, substantial hydrolysis accompanies hydrogenation to ultimately afford the polyols of this invention.

The examples of carbohydrates below are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide which affords a mixture of sorbitol and mannitol as the product. Examples of disaccharides include maltose, cellobiose, sucrose and lactose. Among the more abundant polysaccarides which may be employed in this invention are starch, cellulose and their degradation products.

The materials used as inert supports for zerovalent ruthenium are hydrothermally stable materials, more particularly, refractory inorganic oxides, clays, and mixtures thereof. As used herein, a hydrothermally stable material is one where less than about 15 ppm of metal originating from the material is leached under standard conditions. Standard conditions consist of contacting with mixing 2.5 g material with 50 ml of a 50% aqueous solution of sorbitol or glucose for 24 hours at 130° C. under 135 atmospheres hydrogen. Among the hydrothermally stable supports used as carriers for zerovalent ruthenium in the catalysts of this invention are included alpha-alumina, theta-alumina, titanated alumina, and titania. What is meant by titanated alumina can be found in our application of Ser. No. 411,156, now U.S. Pat. No. 4,413,152.

The hydrothermally stable support is then impregnated with a ruthenium compound which can be reduced by hydrogen to zerovalent ruthenium. Water soluble ruthenium compounds are preferred for convenience in impregnating the support, although this is only a desirable condition and not a necessary one. Among suitable ruthenium compounds may be mentioned ruthenium chloride, ruthenium nitrosyl nitrate, ammonium hexachlororuthenate, ruthenium bromide, ruthenium dodecacarbonyl, potassium ruthenate, and hexammine ruthenium chloride.

After the support is impregnated with a reducible ruthenium compound a common procedure calls for calcination in nitrogen of the resulting impregnate at temperatures in excess of about 350° C. However, I have found that omitting the calcination step prior to reduction with hydrogen affords a somewhat more active catalyst, and in the practice of this invention it is preferred not to calcine the impregnate.

The impregnate then is treated with hydrogen at an elevated temperature so as to reduce the ruthenium compound and produce zerovalent ruthenium. Conventional methodology calls for reduction at a temperature in excess of about 350° C. But the discovery which forms the basis of this invention is that reduction by hydrogen at a temperature from about 100° C. to about 300° C., and more particularly between about 125° C. and about 250° C., affords a more active catalyst than that obtained when the zerovalent ruthenium is produced by reduction at a temperature in excess of about 350° C.

The aqueous solution of the carbohydrate is contacted with hydrogen and the catalyst of this invention at hydrogenation conditions. Hydrogenation conditions include a pressure of at least about 200 psig, with pressures in excess of about 5000 psig generally not advantageous. In the usual case, a hydrogen pressure from about 700 to about 5000 psig is used, with a pressure from about 1000 to about 3000 psig preferred. The hydrogenation temperature will be greater than about 80° C., with the upper temperature limit dictated by the onset of the decomposition of either the product or reactant. For example, in the case of glucose as the reactant and sorbitol as the product, the upper temperature limit is about 160° C. In practical terms, a hydrogenation temperature from about 100° to about 150° C. is preferred with one from about 105° to about 130° C. being especially advantageous.

The amount of catalyst used will depend, inter alia, on the amount of metal on the support, hydrogenation pressure, and temperature. Usually, sufficient catalyst is employed to give from about 0.1 to about 1 wt. % ruthenium based on the carbohydrate as monosaccharide.

The method of this invention may be practiced in either a batch or a fixed mode. In the batch mode, an aqueous solution of the carbohydrate containing from about 25 to about 60 percent carbohydrates is loaded into a reactor containing the ruthenium catalyst of this invention in an amount sufficient to give from about 0.1 to about 1 wt. % ruthenium based on the carbohydrate. The mixture is then heated to the desired temperature, which is from about 80° to about 160° C., and usually from about 100° to about 150° C. After the desired reaction temperature is attained, hydrogen is admitted to a pressure from about 700 to about 5000 psig. The entire reaction mixture is then agitated to provide adequate contact among the hydrogen, catalyst, and carbohydrate. The hydrogenation is continued until there is no further hydrogen uptake, which generally is a time from about 0.5 to about 5 hours.

The invention described is advantageously practiced in a continuous fashion using the catalyst in a fixed bed, fluidized bed, expanded bed, and so forth. In a typical operation, feedstock containing from about 25 to about 60% of the carbohydrate(s) to be reduced is passed through the bed of ruthenium dispersed on a hydrothermally stable support in a hydrogen atmosphere. Hydrogen pressure is from about 700 to about 5000 psig, and bed temperature is generally from about 100° to about 150° C. The effluent is an aqueous solution of the formed polyol(s), which may be recovered, for example, by removal of water by evaporation.

The examples which follow merely illustrate this invention and are not intended to limit it in any way.

EXAMPLE 1

The following description is representative of the preparation of the catalysts of this invention, with the variables being limited to the relative amounts of ruthenium compound and support, the presence or absence of calcination in nitrogen, and the reduction temperature. A solution of 11 g $RuCl_3.3H_2O$ in 280 ml deionized water was mixed with 138 g theta-alumina and water was evaporated with gentle heating. The impregnated alumina was placed in a vertical tube furnace and calcined, if at all, in flowing nitrogen for 3 hours at 400° C., then reduced in flowing hydrogen for 3 hours at 140°, 250°, or 400° C. Catalysts of series A were calcined and reduced at 400° C.; catalysts of series B were not calcined and were reduced at 400° C.; catalysts of series C were not calcined and were reduced at 140° C. Catalysts of series A, B, and C utilized theta-alumina as the inert support.

EXAMPLE 2

The following procedure was used to demonstrate the hydrothermal stability of materials used as an inert support for catalytically active zerovalent ruthenium. A mixture of 50 ml of a 50% aqueous solution of sorbitol or, less frequently, glucose and 2.5 g of support material was held in a rotating glass-lined autoclave for 24 hours in the presence of hydrogen at 135 atmospheres and at 130° C. At the end of this period solid was removed by filtration and the filtrate was analyzed for metals. The following table summarizes the results.

| LEACHING OF INERT SUPPORTS | |
|---|---|
| Support material | Dissolved metal |
| TiO$_2$ —bentonite (ca. 90% TiO$_2$)[a] | less than 1 ppm Ti; 93 ppm Si |
| gamma-alumina[a, b] | 60 ppm Al |
| titanated alumina from above[a, c] | less than 1 ppm Ti; 3.5 ppm Al |
| gamma-alumina[a, d] | 129 ppm Al |
| alpha-alumina[a] | less than 1 ppm Al |
| kieselguhr[e] | 83 ppm Si |

[a]Test solution — sorbitol
[b]0.5 ABD, SA 200 m$^2$/g
[c]0.9% Titanium
[d]0.3 ABD, SA 160 m$^2$/g
[e]Test solution — glucose

EXAMPLE 3

Into a rotating 300 ml. glass-lined autoclave was placed 60 ml. of a 50% aqueous glucose solution and 2.0 g. catalyst. The contents were heated to 100° C., and hydrogen was admittted to a pressure of 35 atmospheres. After 5 hours the contents were cooled, catalyst was removed by filtration, and the filtrate was analyzed by high pressure liquid chromatography for glucose content. The percent glucose conversion was used as a measure of catalyst activity. Data obtained in this way were used to generate the curves in the FIGURE.

What the FIGURE shows is a generally higher conversion, therefore activity, with catalysts of series B than with catalysts of series A. Thus, omission of calcination improved catalyst activity. Catalysts of series C are still more active, showing that reduction of the ruthenium compound at 140° C. affords a catalyst with increased activity.

Using a catalysts of 3% ruthenium on titanated gamma-alumina calcined at 400° C., that prepared by reduction at 400° C. afforded 69% conversion of glucose, whereas that prepared by reduction at 250° C. afforded 75.5% conversion, again demonstrating the increased activity accompanying lower reduction temperature.

What is claimed is:

1. In the method of hydrogenating a carbohydrate in aqueous solution to its polyols comprising contacting at hydrogenation conditions a reaction medium consisting essentially of said solution with hydrogen and a catalyst consisting essentially of zerovalent ruthenium dispersed on a hydrothermally stable support, the improvement wherein the zerovalent ruthenium is produced by reduction of a ruthenium impregnate with hydrogen at a temperature from about 100° C. to about 300° C.

2. The method of claim 1 where the support is selected from the group consisting of alpha-alumina, theta-alumina, titanated alumina, and titania.

3. The method of claim 1 where the carbohydrate is a monosaccharide.

4. The method of claim 3 where the monosaccharide is selected from the group consisting of hexoses, pentoses, and tetroses.

5. The method of claim 3 where the monosaccharide is a hexose and the polyol is a hexitol.

6. The method of claim 5 where the hexose is glucose or mannose and the hexitol is sorbitol or mannitol, respectively.

7. The method of claim 5 where the hexose is fructose and the polyol is a mixture of sorbitol and mannitol.

8. The method of claim 1 where the hydrogenation conditions include a hydrogen pressure from about 700 to about 5000 psig and a temperature from about 80° to about 160° C.

9. The method of claim 1 where the zerovalent ruthenium is produced by reduction at a temperature from about 125° to about 250° C.

10. The method of claim 1 where the impregnate is not calcined.

* * * * *